(12) United States Patent
Kojima

(10) Patent No.: US 10,130,339 B2
(45) Date of Patent: Nov. 20, 2018

(54) ULTRASOUND SENSOR AND METHOD OF MANUFACTURING THEREOF

(71) Applicant: Seiko Epson Corporation, Tokyo (JP)

(72) Inventor: Chikara Kojima, Matsumoto (JP)

(73) Assignee: Seiko Epson Corporation (JP)

( * ) Notice: Subject to any disclaimer, the term of this patent is extended or adjusted under 35 U.S.C. 154(b) by 295 days.

(21) Appl. No.: 15/115,146

(22) PCT Filed: Jun. 30, 2015

(86) PCT No.: PCT/JP2015/003281
§ 371 (c)(1),
(2) Date: Jul. 28, 2016

(87) PCT Pub. No.: WO2016/002206
PCT Pub. Date: Jan. 7, 2016

(65) Prior Publication Data
US 2016/0345934 A1    Dec. 1, 2016

(30) Foreign Application Priority Data

Jun. 30, 2014 (JP) ................................. 2014-135135
Jun. 29, 2015 (JP) ................................. 2015-130396

(51) Int. Cl.
*H01L 41/047* (2006.01)
*A61B 8/00* (2006.01)
(Continued)

(52) U.S. Cl.
CPC .......... *A61B 8/4494* (2013.01); *A61B 8/4427* (2013.01); *A61B 8/4444* (2013.01);
(Continued)

(58) Field of Classification Search
CPC ... A61B 8/4494; A61B 8/4427; A61B 8/4444; H01L 41/047
See application file for complete search history.

(56) References Cited

U.S. PATENT DOCUMENTS 9,184,370 B2    11/2015  Kano
9,846,145 B2 *  12/2017  Yoshimura ......... G01N 29/2406
(Continued)

FOREIGN PATENT DOCUMENTS

JP    2010164331 A    7/2010
JP    2011082624 A    4/2011
(Continued)

*Primary Examiner* — J. San Martin
(74) *Attorney, Agent, or Firm* — Harness, Dickey & Pierce, P.L.C.

(57) ABSTRACT

An ultrasound sensor, including a plurality of ultrasound elements which include a first electrode, a piezoelectric layer, and a second electrode and which are arranged in a first direction and a second direction, in which at least a portion of the plurality of ultrasound elements are grouped, at least one of the first electrode and the second electrode is shared for each of the grouped ultrasound elements, bypass wiring is connected to at least one of the shared first electrode and second electrode, a following α value of the bypass wiring is greater than the α value of the first electrode or second electrode on which the bypass wiring is connected, and the electric resistance value per unit length of the bypass wiring is lower than that of the first electrode or the second electrode.

α value=(Young's modulus of Constituent Material)×(cross-sectional area of wiring or electrode).

9 Claims, 13 Drawing Sheets

(51) Int. Cl.
*H01L 41/113* (2006.01)
*H01L 41/29* (2013.01)
*H04R 17/00* (2006.01)
*H04R 31/00* (2006.01)

(52) U.S. Cl.
CPC .......... *H01L 41/047* (2013.01); *H01L 41/113* (2013.01); *H01L 41/1132* (2013.01); *H01L 41/29* (2013.01); *H04R 17/00* (2013.01); *H04R 31/00* (2013.01)

(56) References Cited

U.S. PATENT DOCUMENTS

| | | |
|---|---|---|
| 2014/0007693 A1 | 1/2014 | Torashima et al. |
| 2015/0009778 A1 | 1/2015 | Kandori et al. |
| 2015/0094590 A1* | 4/2015 | Kiyose ................. B06B 1/0629 600/447 |
| 2015/0094596 A1* | 4/2015 | Kiyose ................. A61B 8/4483 600/472 |
| 2016/0038120 A1 | 2/2016 | Kano |
| 2016/0345932 A1* | 12/2016 | Miyazawa ........... A61B 8/4209 |
| 2017/0157647 A1* | 6/2017 | Kojima ................ B06B 1/0622 |
| 2018/0090666 A1* | 3/2018 | Ohashi ................. H01L 41/042 |

FOREIGN PATENT DOCUMENTS

| | | |
|---|---|---|
| JP | 2012109800 A | 6/2012 |
| JP | 2013106188 A | 5/2013 |
| JP | 2014017564 A | 1/2014 |
| JP | 2014161707 A | 9/2014 |

\* cited by examiner

A-A'

B-B'

C-C'

D-D'

E-E'

F-F' ural Phase Application
ULTRASOUND SENSOR AND METHOD OF MANUFACTURING THEREOF

CROSS-REFERENCE TO RELATED APPLICATIONS

This application is a U.S. National Phase Application under 35 U.S.C. 371 of International Application No. PCT/JP2015/003281, filed on Jun. 30, 2015 and published in Japanese as WO2016/002206 on Jan. 7, 2016. This application claims priority to Japanese Patent Application No. 2014-135135, filed on Jun. 30, 2014 and Japanese Patent Application No. 2015-130396, filed on Jun. 29, 2015. The entire disclosures of the above applications are incorporated herein by reference.

TECHNICAL FIELD

The present invention relates to an ultrasound sensor and a method of manufacturing thereof.

BACKGROUND ART

Ultrasound sensors in which a semiconductor substrate having an opening portion, two layers of electrodes on an insulating film layer formed on the surface of the semiconductor substrate while blocking the opening portion and a PZT ceramic thin film layer interposed between the two layers of electrodes are arranged in an array form are known in the related art (for example, refer to Japanese Unexamined Patent Application Publication No. 2010-164331).

SUMMARY OF INVENTION

Technical Problem

In an ultrasound sensor in which the elements are arranged in such an array form, although the first electrode and the second electrode are shared and drawn out in the row direction, in particular in a shared wiring, the impedance increases and the efficiency of transmission and reception is lowered according to the separation from an external connection terminal along the row direction, and the reliability is lowered.

As long as a soft material such as gold (Au) or copper (Cu) which are generally used electrode materials is used, it is possible to easily form circuits with low electrical resistance and impedance. However, there are constraints on various electrodes which form the element, such as using a hard material with a high Young's modulus in order to ensure the characteristics of the element, and application of the above-described soft materials is not preferred.

Solution to Problem

The invention was created in consideration of the above-described situation and an object thereof is to provide an ultrasound sensor in which impedance is reduced without the characteristics of the element being lowered and for which reliability is improved by efficiently withdrawing a wiring from elements arranged in an array form, and a method of manufacturing thereof.

According to an aspect of the invention, there is provided an ultrasound sensor including a plurality of ultrasound elements which include a first electrode, a piezoelectric layer, and a second electrode and which are arranged in a first direction and a second direction, in which at least a portion of the plurality of ultrasound elements are grouped, at least one of the first electrode and the second electrode is shared for each of the grouped ultrasound elements, bypass wiring is connected to one of the shared first electrode and second electrode, an α value of the bypass wiring is greater than the α value of the first electrode or second electrode to which the bypass wiring is connected, and when electric resistance values per unit length are compared, the electric resistance value of the bypass wiring is lower than the electrical resistance value of the first electrode or the second electrode to which the bypass wiring is connected.

In the aspect, the increase in the impedance of the first electrode or second electrode connected to the bypass wiring can be averaged, transmission and reception can be efficiently performed, and the reliability can be improved by providing bypass wiring having the predetermined α value. The impedance of the first electrode or the second electrode connected to the bypass wiring can be more reliably lowered by stipulating the electrical resistance value of the bypass wiring. Furthermore, the relationship between the α value and the electrical resistance value can be easily satisfied by the bypass wiring using a different material to the constituent material of the first or second electrode.

It is preferable that the bypass wiring is provided above the first electrode or the second electrode in a region in which the bypass wiring and the first electrode or the second electrode are superimposed. Thereby, yield during manufacturing can be improved, and reliability can be improved.

It is preferable that the other of the shared first electrode and the second electrode is also shared, second bypass wiring that is electrically connected to the other of the first electrode or the second electrode is provided, and the α value of the second bypass wiring is greater than that of the first or the second electrode to which the bypass wiring is connected. Accordingly, the impedance of the first or second electrode can be reduced.

According to another aspect of the invention, there is provided a method of manufacturing an ultrasound sensor that includes a plurality of ultrasound elements that include a first electrode, a piezoelectric layer, and a second electrode, and which are arranged in a first direction and a second direction and at least one of the first electrode and the second electrode is shared for each of the plurality of ultrasound elements, the method including forming bypass wiring that is provided with respect to the first electrode or the second electrode after forming the first electrode, the piezoelectric layer, and the second electrode, and for which the α value is greater than the α value of the first electrode or the second electrode and the electrical resistance value per unit length is lower than that of the first electrode or the second electrode.

According to the aspect, the yield during manufacturing can be improved, the impedance of the first or second electrode can be more reliably lowered, and the reliability can be improved.

DESCRIPTION OF EMBODIMENTS

Figure 1:
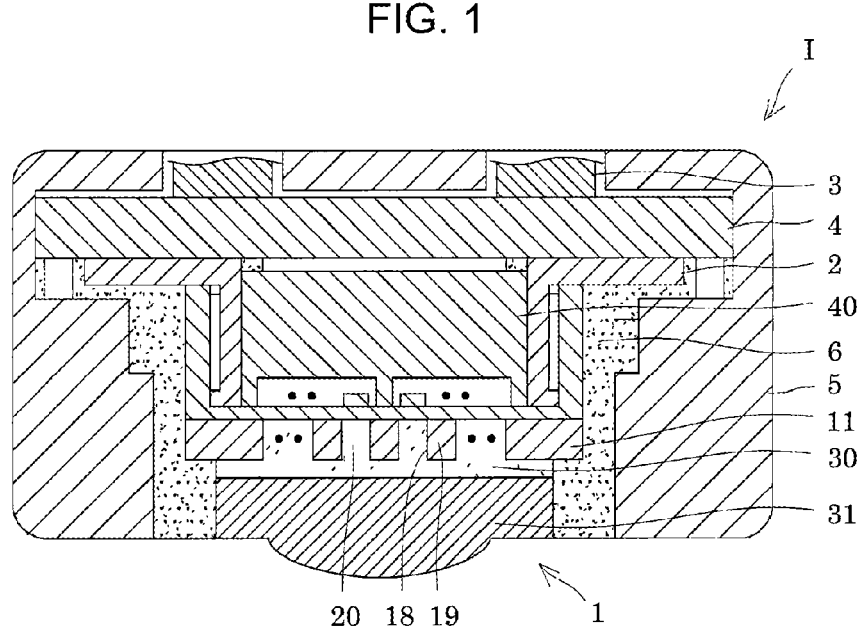
FIG. 1 is a cross-sectional view illustrating a configuration example of an ultrasound device according to Embodiment 1.

Below, embodiments of the invention will be described with reference to the drawings. The description below illustrates one form of the invention, and arbitrary modifications are possible within the scope of the invention. In the respective drawings, portions given the same reference numeral illustrate the same members, and description thereof will not be made, as appropriate.

Embodiment 1

Figure 2:
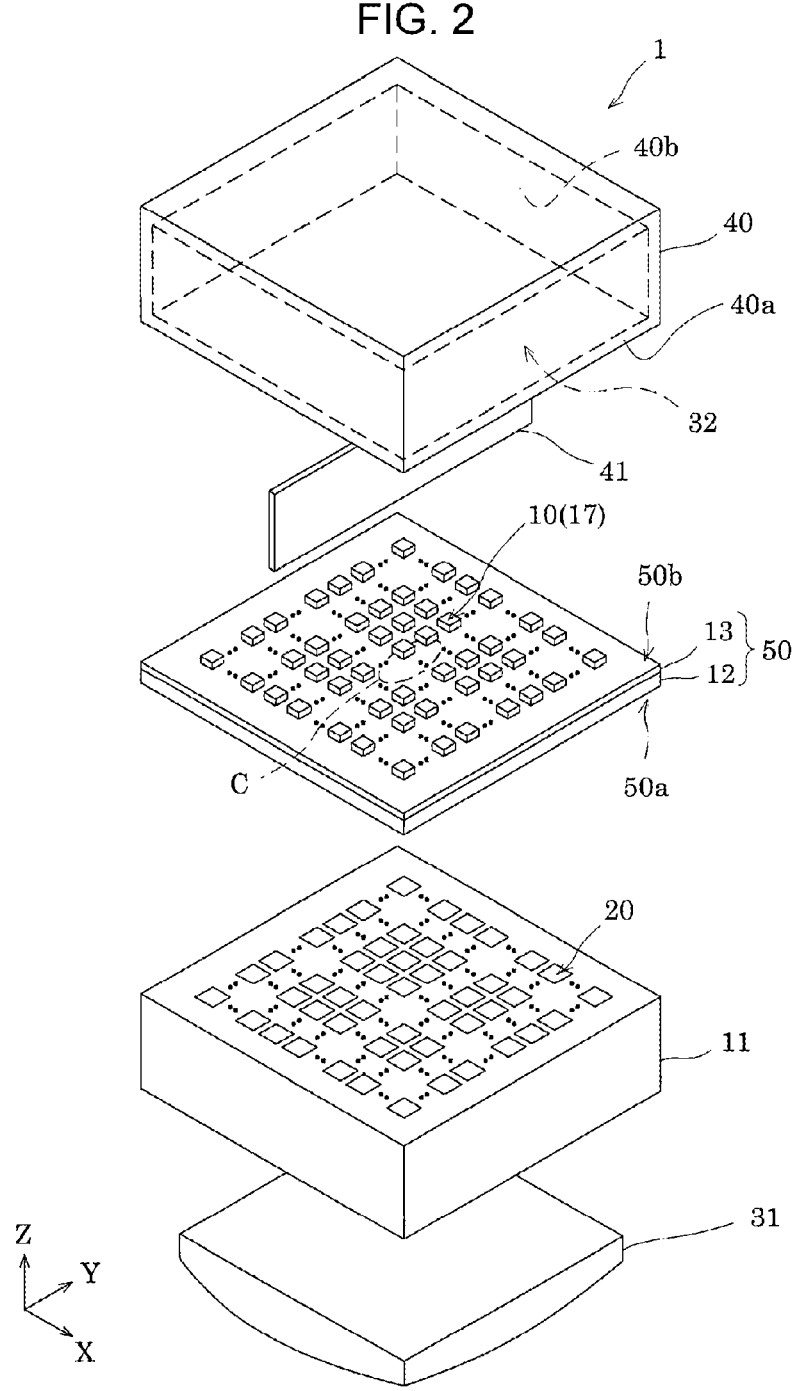
FIG. 2 is an exploded perspective view illustrating a configuration example of an ultrasound sensor according to Embodiment 1.

FIG. 1 is a cross-sectional view illustrating a configuration example of an ultrasound device on which the ultrasound sensor according to Embodiment 1 of the invention is mounted. FIG. 2 is an exploded perspective view of the ultrasound sensor.

As illustrated in FIG. 1, the ultrasound probe I is formed including a CAV surface type ultrasound sensor 1, a flexible printed substrate (FPC substrate 2) connected to the ultrasound sensor 1, a cable 3 drawn out from an apparatus terminal (not shown), a relay substrate 4 that serves as an intermediate between the FPC substrate 2 and the cable 3, a housing 5 that protects the ultrasound sensor 1, the FPC substrate 2 and the relay substrate 4, and a waterproof resin 6 which fills the space between the housing 5 and the ultrasound sensor 1.

Ultrasound waves are transmitted from the ultrasound sensor 1. Ultrasound waves reflected from a measurement target are received by the ultrasound sensor 1. Information (such as position and shape) pertaining to the measurement target is detected in the apparatus terminal of the ultrasound probe I based on the waveform signal of the ultrasound waves.

According to the ultrasound sensor 1, it is possible to ensure high reliability, as described later. Accordingly, by mounting the ultrasound sensor 1, an ultrasound device with various superior characteristics is formed. It is possible to also apply the invention to any ultrasound sensor 1, such as a dedicated transmission type optimized to the transmission of ultrasound waves, a dedicated reception type optimized to the reception of ultrasound waves, and a transmission and reception integrated type optimized to the transmission and reception of ultrasound waves. The ultrasound device on which the ultrasound sensor 1 is able to be mounted is not limited to the ultrasound probe I.

As illustrated in FIGS. 1 and 2, the ultrasound sensor 1 is formed including an ultrasound sensor element 10, an acoustic matching layer 30, a lens member 31, and an enclosure plate 40. The ultrasound sensor element 10 is formed including a substrate 11, a diaphragm 50, and a piezoelectric element 17. In FIG. 2, although the enclosure plate 40 and the support member 41 are depicted as separate bodies, in practice, both are integrally formed.

When two mutually orthogonal axes are the X-axis and the Y-axis and the plane formed by the X-axis and the Y-axis is the XY-plane, the substrate 11 follows the XY-plane. Below, the X-axis is referred to as the first direction X, the Y-axis as the second direction Y, and the Z-axis direction which is orthogonal to both of the first direction X and the second direction Y as the third direction Z.

As illustrated in FIG. 1, a plurality of dividing walls 19 are formed on the substrate 11. A plurality of spaces 20 are divided along the first direction X and the second direction Y by the plurality of dividing walls 19. The spaces 20 are formed so as to pass through the substrate 11 in the third direction Z. The spaces 20 are formed in a two-dimensional form, that is, a plurality in the first direction X and a plurality in the second direction Y. The arrangement or shape of the spaces 20 can be modified in various ways. For example, the spaces 20 may also be formed in a one-dimensional form, that is, along one direction of either of the first direction X and the second direction Y. The spaces 20 may also have a long shape (a ratio of lengths in the first direction X and the second direction Y other than 1:1) when viewed from the third direction Z.

An acoustic matching layer 30 is provided in the space 20. It is possible to prevent the acoustic impedance between the piezoelectric element 17 and the measurement target from changing suddenly by providing the acoustic matching layer 30 with the opening portion 18 or the like of the substrate 11 being filled with a resin or the like having an acoustic matching capacity, and, as a result, it is possible to prevent the transmission efficiency of the ultrasound waves from being lowered. Although it is possible for the acoustic matching layer 30 to be formed of silicone oil, a silicone resin or a silicone rubber, it is possible to use a material selected, as appropriate, according to the use or the like of the ultrasound sensor without being limited to the examples.

The lens member 31 is provided on the substrate 11 on the opposite side to the diaphragm 50. The lens member 31 has a role of causing the ultrasound waves to converge. In cases such as causing the ultrasound waves to converge with an electronic focusing method, the lens member 31 need not be included. Here, the acoustic matching layer 30 has a function of adhering the lens member 31 and the substrate 11 to each other. The acoustic matching layer 30 is inserted between the lens member 31 and the substrate 11 (dividing wall 19), and the ultrasound sensor 1 is formed.

When the lens member 31 is mounted in the ultrasound sensor element 10 or when the adhesiveness of the lens member 31 is ensured after mounting of the lens member 31, the lens member 31 may be pressed to the acoustic matching layer 30 side. Even in cases where the lens member 31 is not included or another member is provided instead of the lens member, because the adhesiveness of each member is ensured, a pressing force is applied to the diaphragm 50 from the acoustic matching layer 30 side. In the ultrasound sensor 1, because the configuration includes a support member 41, even if a predetermined external pressure is imparted on the diaphragm 50, as described above, it is possible to suppress the occurrence of structural distortion, and it is possible to ensure high reliability.

The diaphragm 50 is provided on the substrate 11 so as to block the space 20. Below, the surface on the substrate 11 side of the diaphragm 50 is referred to as the first surface 50a, and the surface facing the first surface 50a is referred to as the second surface 50b. The diaphragm 50 is formed of an elastic film 12 formed on the substrate 11 and an insulator film 13 formed on the elastic film 12. In this case, the first surface 50a is formed of the elastic film 12 and the second surface 50b of the insulator film 13.

The enclosure plate 40 is provided on the second surface 50b of the diaphragm 50. A concave portion (piezoelectric element holding section 32) is formed in the center of the enclosure plate 40, and the periphery of the piezoelectric element holding section 32 forms the edge portion 40a (refer to FIG. 2 and the like) of the enclosure plate 40. The peripheral region (region that includes the upper surface and the side surface of the piezoelectric element 17) of the piezoelectric element 17 is covered by the piezoelectric element holding section 32. Accordingly, the surface corresponding to the bottom surface of the piezoelectric element holding section 32 becomes the surface 40b on the piezoelectric element 17 side of the enclosure plate 40.

The enclosure plate 40 is bonded to the ultrasound sensor element 10 side in the edge portion 40a. Although it is possible to use an adhesive (not shown) for the bonding of the enclosure plate 40, there is no limitation to this example. Although the depth of the piezoelectric element holding section 32, that is, the length in the third direction Z is approximately 80 µm, there is no limitation to this value. The depth of the piezoelectric element holding section 32 may be a value at which space sufficient to not impede the driving of the piezoelectric element 17 is ensured. The piezoelectric element holding section 32 may be filled with air or may be filled with resin. Although the thickness of the enclosure plate 40 is approximately 400 µm, there is no limitation to this value.

In the ultrasound sensor 1, the support member 41 is provided between the surface 40a of the piezoelectric element 17 of the enclosure plate 40 and the second surface 50b of the diaphragm 50 and at a position not overlapping the piezoelectric element 17. Accordingly, it is possible to support the diaphragm 50 with the support member 41. Therefore, for example, when the lens member 31 is mounted, or when the adhesiveness of the lens member 31 is ensured after mounting of the lens member 31, the diaphragm 50 is prevented from flexing greatly in the piezoelectric element holding section 32 even if a predetermined force is imparted to the diaphragm 50 from the acoustic matching layer 30 side. Thus, it is possible to suppress the occurrence of structural distortion and ensure high reliability.

The support member 41 is provided at a position not overlapping the piezoelectric element 17. Therefore, the piezoelectric element 17 being excessively constrained by the support member 41 is avoided. Thus, the transmission efficiency or reception efficiency of the ultrasound waves is also prevented from being excessively lowered compared with a case where the support member 41 is not provided.

The expression "a position not overlapping the piezoelectric element 17", indicates a position that does not overlap the active portion (portion interposed between the first electrode 14 and the second electrode 16) when viewed from the third direction Z. In particular, in the ultrasound sensor 1, the support member 41 with a narrower width than the dividing wall 19 is provided between adjacent spaces 20. That is, in the ultrasound sensor 1, the support member 41 does not even overlap the movable portion (portion corresponding to the space 20 for the second surface 50b side of the diaphragm 50) when viewed from the third direction Z. Therefore, excessive lowering of the transmission efficiency or reception efficiency of the ultrasound waves is reliably prevented compared to a case where the support member 41 is not provided. Although the support member 41 is bonded to the ultrasound sensor element 10 side by an adhesive (not shown), the bonding method is not limited to the previous example.

The support member 41 has a beam shape which extends along the second direction Y. Accordingly, it is possible to support the diaphragm 50 over a wide range which spans the second direction Y. The beam-like support member 41 may extend along the first direction X, rather than the first direction X. For the beam-like support member 41, the one end portion which extends may be separated from the edge portion 40a of the enclosure plate 40. If at least one end portion in the extension direction contacts the edge portion 40a of the enclosure plate 40, the one end portion is pinched by the beam-like support member 41.

The beam-like support member 41 is prepared by wet etching the enclosure plate 40. In this way, the support member 41 is prepared by taking advantage of the constituent material of the enclosure plate 40 and has the same configuration as the enclosure plate 40. Because it is possible for a large region to be removed in a short time, even though the work precision deteriorates compared to, for example, dry etching, wet etching is a method suitable for preparing the beam-like support member 41.

The central portion of the piezoelectric element holding section 32 is comparatively separated from the edge portion 40a of the enclosure plate 40. Accordingly, in the central location C (refer to FIG. 2 or the like) corresponding to the central portion of the piezoelectric element holding section 32, the rigidity in the diaphragm 50 has a tendency to decrease in a case where there is no support member 41. Here, the support member 41 is provided so as to support the central location C of such a diaphragm 50. In so doing, it is possible to ensure higher reliability.

In the invention, the number, arrangement, shape, and the like of the support member can be selected in various ways. For example, a plurality of support members 41 may be provided. In this case, it is preferable that the support member 41 is provided at equal intervals in the piezoelectric element holding section 32. Accordingly, it is possible to evenly support the diaphragm 50. Accordingly, it is preferable that the number of diaphragms 50 be an odd number of three or more. This is because, when the support members 41 are provided at equal intervals in the piezoelectric element holding section 32, the support member 41 at the center thereof is able to be positioned in the vicinity of the central location C of the diaphragm 50. For example, when the number of support members 41 is approximately three, the balance is good.

The support member 41 may be provided only at a portion shifted from the central location C of the diaphragm 50. The support member 41 need not have a beam shape. The support member 41 need not have a linear shape in the extension direction. Even though there are cases where the method of preparing the support member 41 has a form in which the cross-sectional area of the XY plane of the support member 41 is different according to the third direction Z, as long that the form is able to support the diaphragm 50, the form is also included in the support member 41 of the invention.

Figure 3:
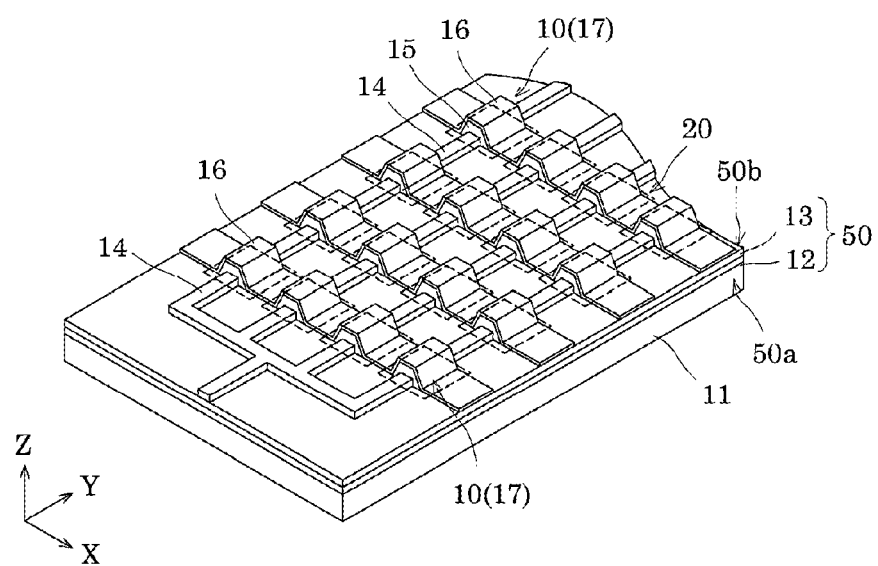
FIG. 3 is an enlarged perspective view illustrating a configuration example of an ultrasound sensor element array.
Figure 4:
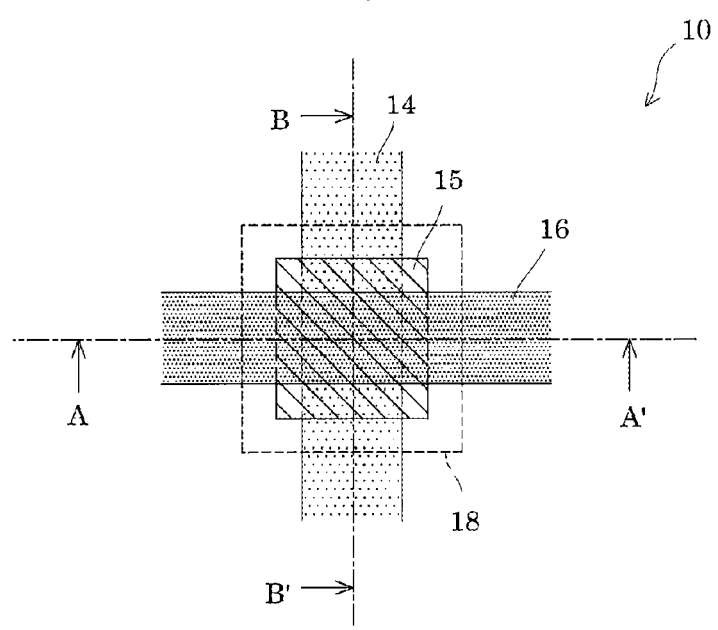
FIG. 4 is a plan view illustrating a schematic configuration of an ultrasound sensor element according to Embodiment 1.
Figure 4:
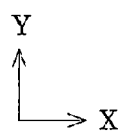
Figure 5:
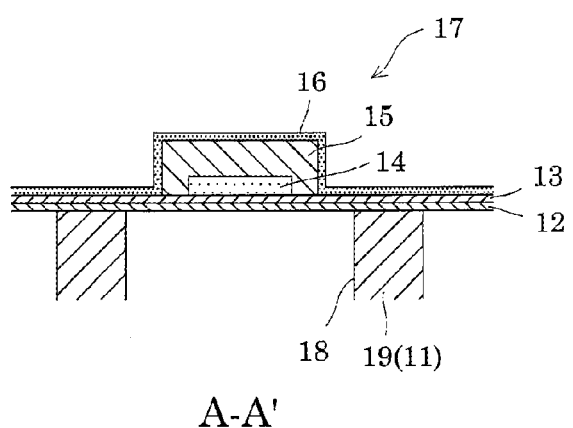
FIGS. 5(a) and 5(b) show cross-sectionals of the ultrasound sensor element according to Embodiment 1.
Figure 5:
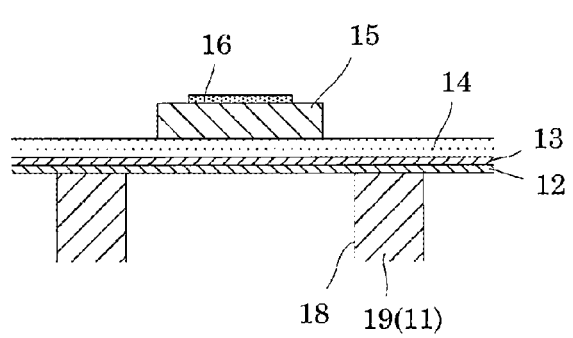
Figure 6:
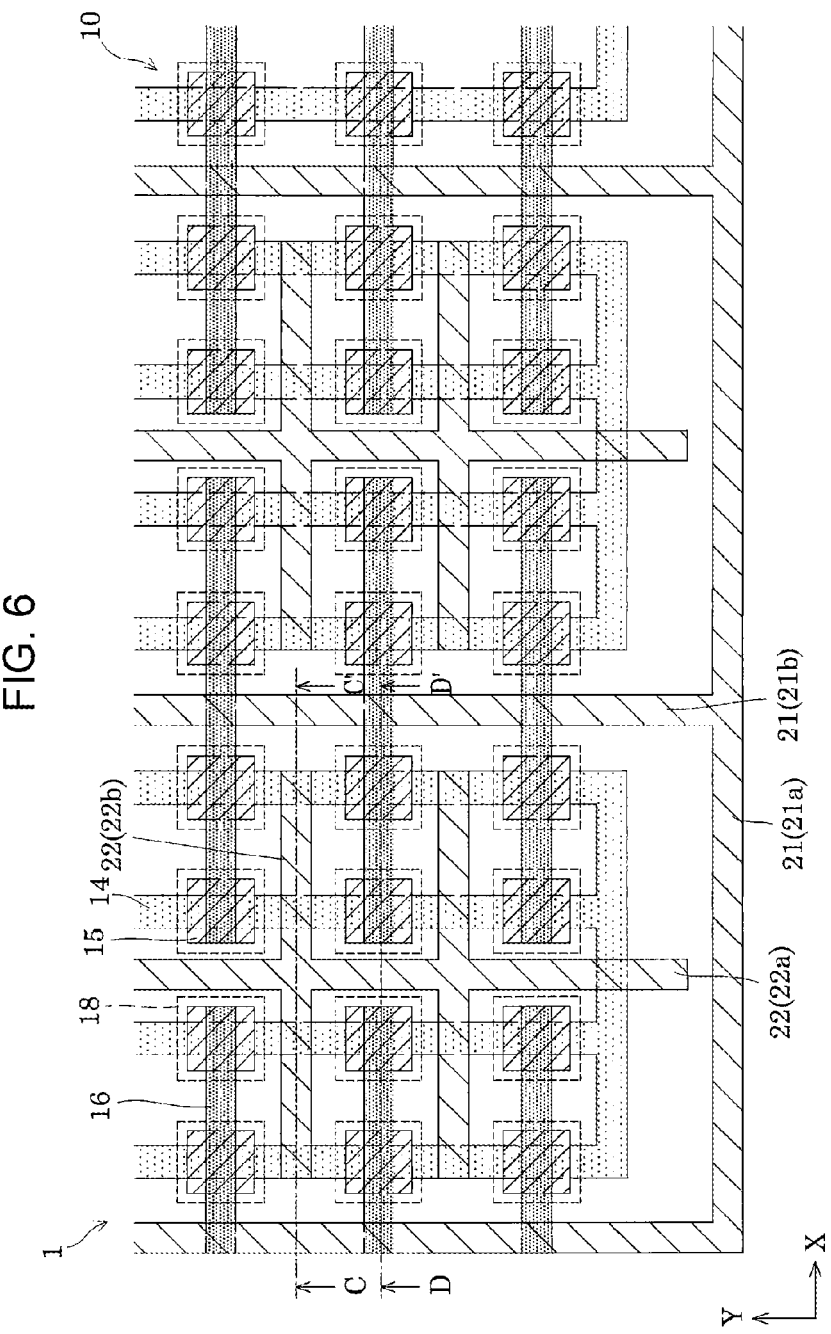
FIG. 6 is a plan view illustrating a schematic configuration of the ultrasound sensor according to Embodiment 1.
Figure 7A:
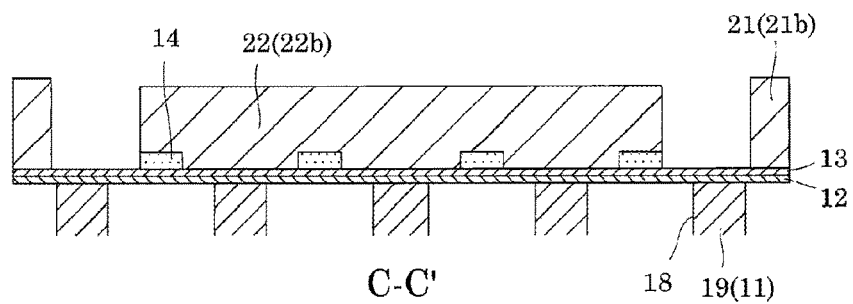
FIGS. 7(a) and 7(b) show cross-sectionals of the ultrasound sensor according to Embodiment 1.
Figure 7B:
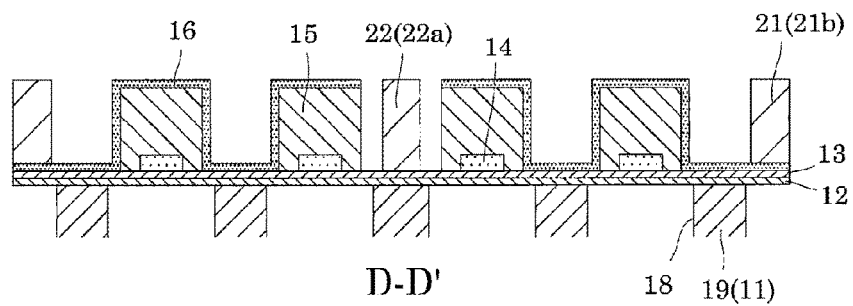
Figure 8:
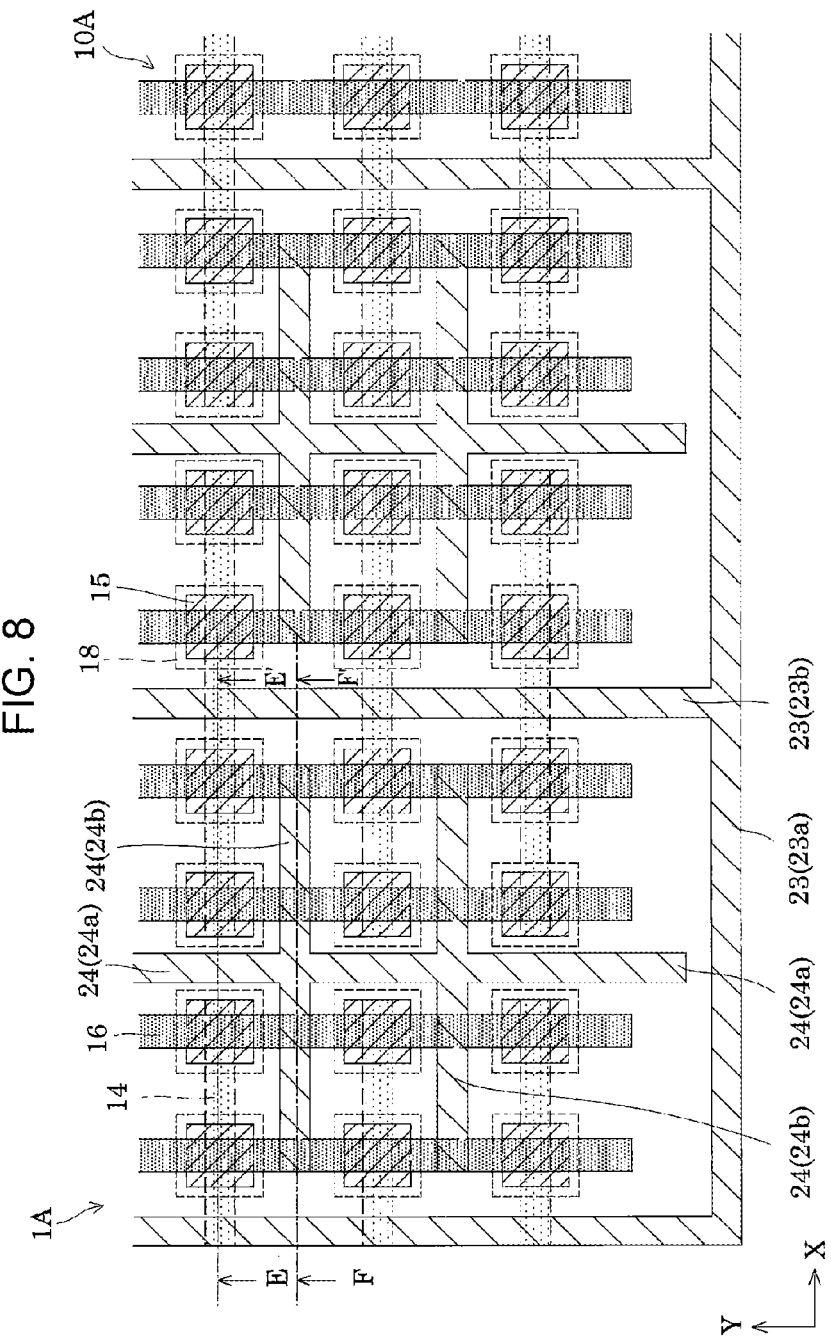
FIG. 8 is a plan view illustrating a schematic configuration of an ultrasound sensor according to Embodiment 2.
Figure 9A:
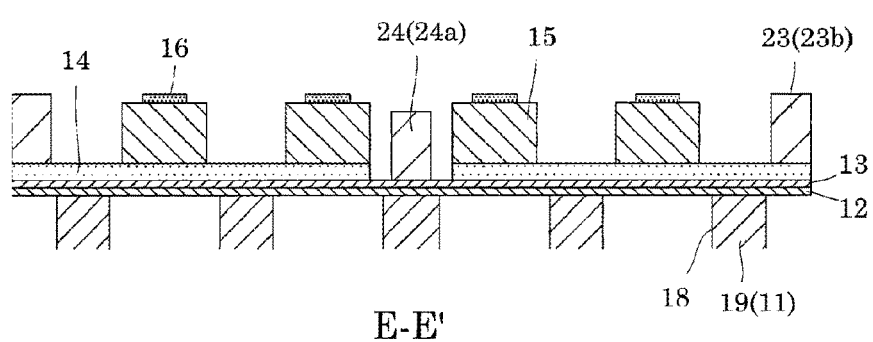
FIGS. 9(a) and 9(b) show cross-sectionals of the ultrasound sensor according to Embodiment 2.
Figure 9B:
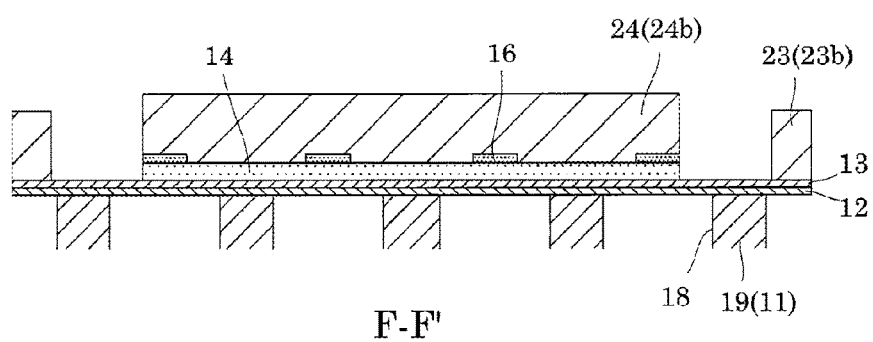

FIG. 3 is an enlarged perspective view illustrating a configuration example of an ultrasound sensor element array. FIG. 4 is a cross-sectional view illustrating a schematic configuration of the ultrasound sensor element according to Embodiment 1 of the invention, FIG. 5(a) is a cross-sectional view taken along line A-A' and FIG. 5(b) is a cross-sectional view taken along line B-B', FIG. 6 is a plan view illustrating a schematic configuration of the ultrasound sensor, and FIG. 7(a) is a cross-sectional view taken along C-C' and FIG. 7(b) is a cross-sectional view taken along line D-D'.

The ultrasound sensor element 10 of the embodiment is formed of an elastic film 12 formed of a silicon dioxide film provided on one surface of the substrate 11 formed of a silicon substrate and a piezoelectric element 17 which is formed on an insulator film 13 formed of zirconium oxide and which formed of a first electrode 14, a piezoelectric layer 15, and a second electrode 16. An opening portion 18 is formed in a region corresponding to the piezoelectric element 17 of the substrate 11, and the opening portion 18 is divided by a dividing wall 19.

Although it is possible to use a single-crystal silicon substrate as the substrate 11, there is no limitation thereto. In the embodiment, although the diaphragm 50 is configured by an elastic film 12 formed of silicon dioxide or the like and an insulator film 13 formed of zirconium oxide or the like, there is no limitation thereto, and either one may be used or another film may be used.

The piezoelectric element 17, which is formed of a first electrode 14, a piezoelectric layer 15 with a thin film thickness of 3 μm or less and preferably 0.3 to 1.5 μm, and a second electrode 16 with an adhesive layer interposed as necessary, is formed on the insulator film 13. Here, the piezoelectric element 17 refers to the portion that contains the first electrode 14, the piezoelectric layer 15, and the second electrode 16.

In general, in a case of driving the piezoelectric element 17, although either one of the electrodes is a common electrode and the other electrode is an individual electrode, in the ultrasound sensor element 10, since driving and scanning are performed for each plurality of ultrasound sensor elements 10, it is not realistic to distinguish which one is the common electrode and which is the individual electrode. In any case, in a case of using a form in which the ultrasound sensor elements 10 are arranged one-dimensionally or two-dimensionally, it is possible to drive only a predetermined piezoelectric element 17 by providing the first electrode 14 so as to span in one direction, provide the second electrode 16 so as to span in a direction orthogonal to the one direction, and applying a voltage between the first electrode 14 and the second electrode 16 selected, as appropriate. When selecting the predetermined piezoelectric element 17, the driving is generally performed by selecting one row or a plurality of rows as one group. In the embodiment, four rows of the first electrodes 14 are bound and shared. This is tentatively referred to as 1-channel, and a plurality of channels are provided spanning the first direction X. The second electrode 16 is continuously provided as one row along the first direction X, and a plurality of rows is provided along the second direction Y.

In such a configuration, when all rows of the second electrodes 16 are shared, all of the piezoelectric elements 17 in the 1-channel are driven at the same time and each channel is driven sequentially, it is possible to acquire data of one dimension along the first direction X.

When the second electrodes 16 are shared one row at a time or a plurality of rows at a time, the piezoelectric elements 17 in 1-channel are shared by the second electrodes 16 and sequentially driven a group at a time, and each channel is sequentially driven, it is possible to acquire two-dimensional data in the XY direction.

Hereafter, the combination of the piezoelectric element 17, and the elastic film 12 and the insulator film 13 which are the diaphragm 50 in which displacement occurs due to driving of the piezoelectric element 17 are referred to as an actuator apparatus. In the above-described examples, although the elastic film 12 and the insulator film 13, the adhesive layer which is provided as necessary, and the first electrode 14 act as the diaphragm 50, there is no limitation thereto. For example, the diaphragm 50 need not be provided, and the piezoelectric element 17 itself may substantially serve as the diaphragm.

The first electrode 14 and the second electrode 16 are not limited as long as they have conductivity and it is possible to use metal materials, such as platinum (Pt), iridium (Ir), gold (Au), aluminum (Al), copper (Cu), titanium (Ti), and stainless steel; tin oxide-based conductive materials, such as indium tin-oxide (ITO), and fluorine-doped tin oxide (FTO); zinc-oxide-based conductive materials, conductive oxides, such as strontium ruthenate ($SrRuO_3$), lanthanum nickelate ($LaNiO_3$), element doped strontium titanate; and conductive polymers. However, there is no restriction to these materials.

It is possible to use a complex oxide with a lead zirconate titanate (PZT)-based perovskite structure for the piezoelectric layer 15, as a representative. Thereby, the displacement amount of the piezoelectric element 17 is easily ensured.

The piezoelectric layer 15 does not include lead, and, for example, it is possible to use a complex oxide with a perovskite structure which includes at least bismuth (Bi), barium (Ba), iron (Fe), and titanium (Ti). Thereby, it is possible to realize an ultrasound sensor element 10 using a non-lead based material with a low load on the environment.

The A site of such a perovskite structure, that is, an ABO3 type structure, is coordinated with 12 oxygen atoms, and, in addition, the B site is coordinated with 6 oxygen atoms, thereby forming an octahedron. In the example of the above-described piezoelectric layer 15 which does not contain lead, the Bi, Ba, and Li are positioned at the A site and the Fe and Ti at the B site.

In the complex oxide which includes a perovskite structure including Bi, Ba, Fe, and Ti, although the constitution formula is represented by $(Bi, Ba)(Fe, Ti)O_3$, a representative constitution is represented as a mixed crystal of bismuth ferrate and barium titanate. The bismuth ferrite and barium titanate of the mixed crystal are not detected singly in an X-ray diffraction pattern. Constitutions deviating from the constitution of the mixed crystal are also included.

Constitutions shifted from the stoichiometric constitution due to lack or excess or in which a portion of the elements are substituted with other elements are also included in the complex oxide with a perovskite structure. That is, as long as a perovskite structure is obtainable, the inevitable deviations in the constitution due to lattice mismatching, oxygen faults and the like such as partial substitution of elements are naturally also permissible.

The configuration of the complex oxide with a perovskite structure is not limited to the examples, and the configuration may include other elements. It is preferable that the piezoelectric layer 15 further include manganese (Mn). Thereby, leakage current is suppressed and it is possible to realize a high-reliability ultrasound sensor element 10 as a non-lead based material.

Bi at the A site of the piezoelectric layer 15 may be substituted with lithium (Li), samarium (Sm), cerium (Ce) or the like, and the Fe at the B site may be substituted with aluminum (Al), cobalt (Co), the like. Thereby, various characteristics are improved, thereby easily achieving diversification of the configuration and function. Even in the case of a compound oxide including these other elements, it is preferable that the configuration have a perovskite structure.

As illustrated in FIGS. 3 and 6, the ultrasound sensor elements 10 of the ultrasound sensor 1 are arranged two-dimensionally in the first direction X and the second direction Y orthogonal thereto, and the first direction X and the second direction Y are the scanning direction and the slice direction, respectively. In the configuration example illustrated in FIG. 3 and the embodiment illustrated in FIG. 6, although 16 ultrasound sensor elements 10 are arranged in the second direction Y which is the slice direction, and 64 ultrasound sensor elements 10 are arranged in the first direction X which is the scanning direction, only a portion of each is illustrated in FIGS. 3 and 6. In such an ultrasound sensor 1, it is possible to continuously acquire, in the scanning direction, sensing information in the slice direction by performing driving, that is, performing transmission and reception of ultrasonic waves for each row extending in the slice direction while scanning in the scanning direction.

In the configuration example in FIG. 3, the first electrode 14 is shared for each row extending in the second direction Y, that is, in the slice direction, and in the embodiment, is shared for every four rows, and driving is possible for every one channel of four rows. Meanwhile, the second electrodes 16 are continuously provided for each row which extends in the first direction X, that is, in the scanning direction, and all of the rows are shared and connected. For the embodiment illustrated in FIG. 6, although the detailed structure for utilizing the bypass wirings 21 and 22, described later, are different, the basic concept and driving method pertaining to the sharing of the electrode are the same as the configuration example in FIG. 3.

In such an ultrasound sensor 1, although an external connection terminal is provided on one or both ends in the first direction X or the second direction Y, the impedance of each electrode is increased according to the distance by which the electrode is separated from the external connection terminal.

In the embodiment, the ultrasound elements 10 are grouped four at a time as illustrated in FIG. 6, and the second electrode 16 is shared for each group of four ultrasound elements. The bypass wiring 21 is connected to the second electrode 16 shared in this way. The bypass wiring 21 is connected to the second electrode 16 and supplements the increase in the impedance of the second electrode 16 in the scanning direction and the slice direction. The bypass wiring 21 includes a first extension section 21a which extends in the first direction X and a second extension section 21b which extends in the second direction Y from the first extension section 21a. A first extension section 21a is provided on both sides in the second direction Y, and the second extension section 21b is provided between each four rows in the first direction X to link the first extension sections 21a.

Such bypass wiring 21 is formed of a different material to the second electrode 16 after patterning of the second electrode 16, as described in detail later. In bypass wiring formed at the same time by the thin film manufacturing process of the ultrasound sensor element 10, it is difficult to form a wiring with a free film thickness, and the width of wiring is also not free. Problems also arise in processes such as film-thinning of the lower layer when patterning the upper layer, and it is difficult to form a wiring with a low impedance. Through manufacturing with a separate process to the thin-film manufacturing process of the ultrasound sensor element 10, it is possible for the yield through manufacturing to be improved and possible to form the wiring with different materials and cross-sectional areas to the first electrode 14 and the second electrode 16.

It is preferable to use a material different to the first and second electrodes 14 and 16, and preferably a material with a low electrical resistivity as the bypass wiring 21, and possible examples include silver, copper, aluminum, and the like. Here, the expression "different material" signifies that the main components which configure the materials (component which accounts for 50% or more of the components) are different. In the embodiment, gold is used. In a case of forming a gold wiring, although a base layer or the like is formed as a base, description of the base layer is not provided in the following description. It is not necessary that the bypass wiring 21 be a single layer, and may be a layered film of two or more layers, and in a case of layering, it is preferable that the overall electric resistance value be smaller than the second electrode 16.

For the bypass wiring 21, it is possible to reduce the impedance of the bypass wiring 21 while suppressing a lowering of the displacement of the piezoelectric element 17 due to the wiring by making the product of the Young's modulus of the material which forms the wiring and the cross-section area of the wiring (below, also referred to as the α value) greater than the α value of the material which forms the shared second electrode 16, and making the electric resistance value (below, also referred to simply as electric resistance value) per unit length of the material which forms the wiring lower than the value of the electric resistance of the material which forms the shared second electrode 16.

In the embodiment, the ultrasound elements 10 are grouped four rows at a time as illustrated in FIG. 6, and the first electrode 14 is shared for each group of four rows of ultrasound elements. The second bypass wiring 22 is connected to the first electrode 14 shared in this way. The second bypass wiring 21 improves the increase in impedance in the extension direction of the first electrode 14 shared for each four rows. The second bypass wiring 22 is provided with a first extension section 22a which extends in the second direction Y which is the extension direction of the first electrode 14 and a second extension section 22b which links the first extension section 22a and the first electrode 14 of each row.

Such second bypass wiring 22 is formed of a different material to the first electrode 14 after patterning of the first electrode 14 and the second electrode 16 similarly to the bypass wiring 21. In forming the bypass wiring at the same time with the thin film manufacturing process of the ultrasound sensor element 10, it is difficult to form a wiring with a free film thickness, and the width of wiring is also not free. Problems also arise in processes such as film-thinning of the lower layer when patterning the upper layer, and it is difficult to form a wiring with a low impedance. Through manufacturing with a separate process to the thin-film manufacturing process of the ultrasound sensor element 10, it is possible for the yield through manufacturing to be improved and possible to form the wiring with different materials and cross-sectional areas to the first electrode 14 and the second electrode 16.

Similarly to the bypass wiring 21, it is preferable to use a material different to the first and second electrodes 14 and 16, and preferably a material with low electrical resistivity, as the bypass wiring 22, and possible examples include silver, copper, aluminum and the like. In the embodiment, gold is used. In a case of forming a gold wiring, although a base layer or the like is formed as a base, description of the base layer is not provided in the following description. It is not necessary that the second bypass wiring 22 be a single layer, and the second bypass wiring 22 may be a layered film of two or more layers, and in a case of layering, it is preferable that the overall electric resistance value be smaller than the first electrode 14.

For the second bypass wiring 22, it is possible to reduce the impedance of the second bypass wiring 22 while suppressing a lowering of the displacement of the piezoelectric element 17 by making the α value larger than that of the shared first electrode 14 and making the electric resistance value smaller than that of the shared first electrode 14.

The second bypass wiring 22 is not necessarily provided, and even if only the bypass wiring 21 is provided, it is possible to reduce the impedance in the scanning direction, as described above.

Embodiment 2

FIG. 58 is a plan view illustrating a schematic configuration of the ultrasound sensor according to Embodiment 2 of the invention, and FIGS. 69(a) and 69(b) are cross-sectional views taken along line E-E' and F-F", respectively.

The ultrasound sensor element 10A of the embodiment includes a wiring by which all of the first electrodes 14 are all shared via bypass wiring 23, and since the other configurations are basically the same as in Embodiment 1, the same configurations are given the same references and overlapping description will not be provided.

In the embodiment, the ultrasound elements 10A are grouped four at a time in the X direction, and the first electrode 14 is shared for each group of four ultrasound elements. The first electrode 14 extends in the first direction X which is the scanning direction. The bypass wiring 23 is connected to the first electrode 14 shared in this way. The bypass wiring 23 is connected to the first electrode 14 and supplements the increase in the impedance of the first electrode 14 in the scanning direction and the slice direction. The bypass wiring 23 includes a first extension section 23a which extends in the first direction X and a second extension section 23b which extends in the second direction Y from the first extension section 23a. A first extension section 23a is provided on both sides in the second direction Y, and the second extension section 23b is provided between each four rows in the first direction X to link the first extension section 23a.

Such bypass wiring 23 is formed of a different material to the first electrode 14 after patterning of the first electrode 14 and the second electrode 16 similarly to the above-described bypass wiring 21. In bypass wiring formed at the same time by the thin film manufacturing process of the ultrasound sensor element 10A, it is difficult to form a wiring with a free film thickness, and the width of wiring is also not free. Problems also arise in processes such as film-thinning of the lower layer when patterning the upper layer, and it is difficult to form a wiring with a low impedance. Through manufacturing with a separate process to the thin-film manufacturing process of the ultrasound sensor element 10A, it is possible for the yield through manufacturing to be improved and possible to form the wiring with different materials and cross-sectional areas to the first electrode 14 and the second electrode 16. The bypass wiring 23 may be provided with the same material and configuration as the bypass wiring 21.

In the embodiment, the ultrasound elements 10A are grouped four rows at a time, and the second electrode 16 is shared for each group of four rows of ultrasound elements. The second electrode 16 extends along the slice direction. The second bypass wiring 24 is connected to the second electrode shared in this way. The second bypass wiring 24 improves the increase in impedance in the extension direction of the second electrode 16 shared for each four rows. The second bypass wiring 24 is provided with a first extension section 24a which extends in the second direction Y which is the extension direction of the second electrode 16 and a second extension section 24b which links the first extension section 24a and the second electrode 16 of each row.

Such second bypass wiring 24 is formed of a different material to the second electrode 16 after patterning of the second electrode 16 similarly to the bypass wiring 21. In bypass wiring formed at the same time by the thin film manufacturing process of the ultrasound sensor element 10A, it is difficult to form a wiring with a free film thickness, and the width of wiring is also not free. Problems also arise in processes such as film-thinning of the lower layer when patterning the upper layer, and it is difficult to form a wiring with a low impedance. Through manufacturing with a separate process to the thin-film manufacturing process of the ultrasound sensor element 10A, it is possible for the yield through manufacturing to be improved and possible to form the wiring with different materials and cross-sectional areas to the first electrode 14 and the second electrode 16. The second bypass wiring 24 may be provided with the same material and configuration as the bypass wiring 21.

Figure 10:
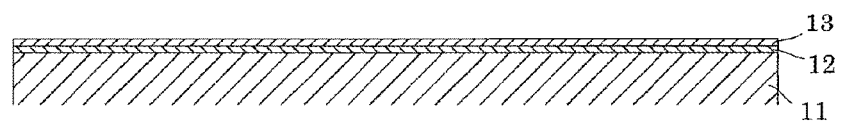
FIGS. 10(a), 10(b) and 10(c) illustrate a manufacturing example of the ultrasound sensor according to Embodiment 1.
Figure 10:
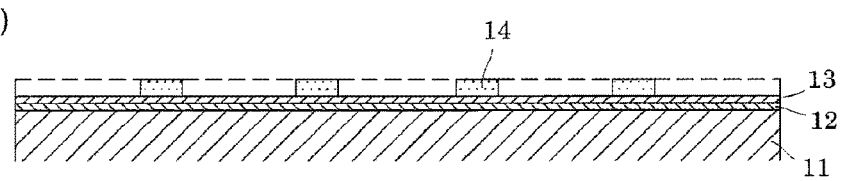
Figure 10:
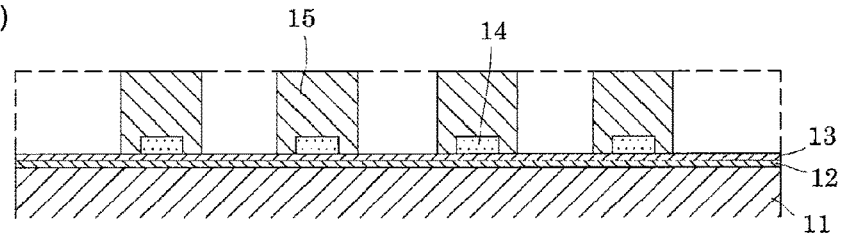
Figure 11:
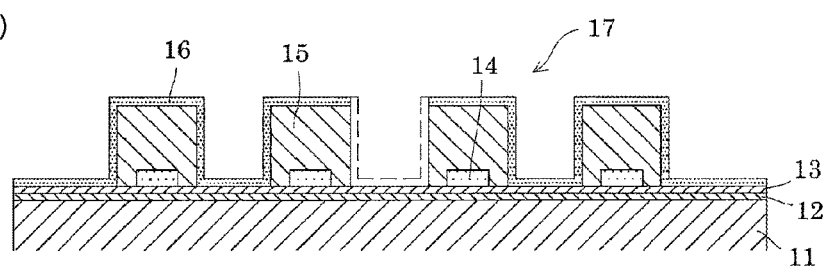
FIGS. 11(a), 11(b) and 11(c) illustrate a manufacturing example of the ultrasound sensor according to Embodiment 1.
Figure 11:
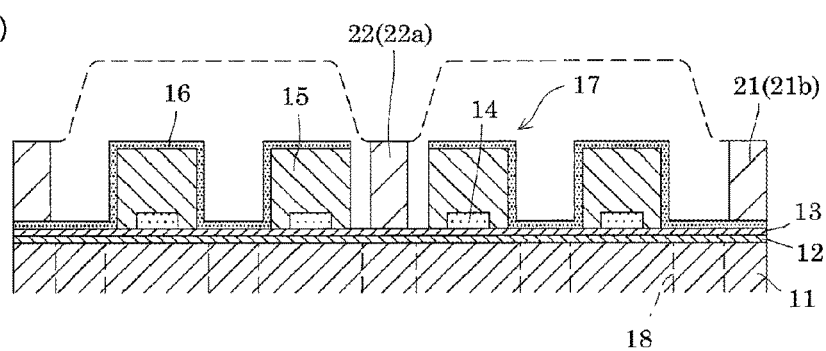
Figure 11:
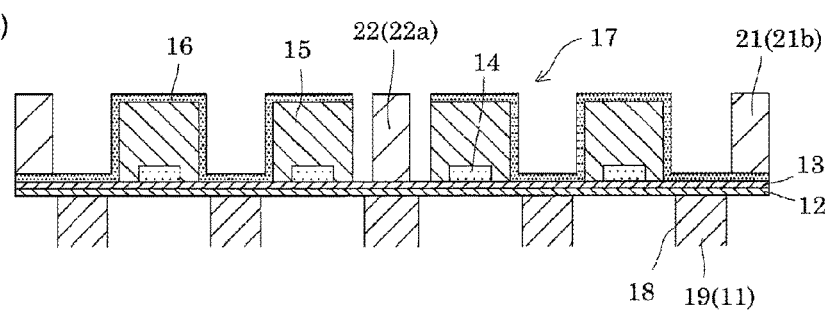

Next, an example of the method of manufacturing the ultrasound sensor of Embodiment 1 will be described with reference to FIGS. 10(a) to 10(c) and 11. FIGS. 10(a) to 10(c) are cross-sectional views illustrating a manufacturing examples of the ultrasound sensor, and correspond to cross-sectional views taken along line D-D' in FIG. 6.

First, as illustrated in FIG. 10(a), after forming an elastic film 12 formed of silicon oxide by thermal oxidation or the like of a substrate 11, a zirconium film is formed thereupon, and thermally oxidized at 500 to 1200° C., and an insulator film 13 formed of zirconium oxide is formed. As illustrated in FIG. 10(b), the first electrode 14 is formed on the insulator film 13 by a sputtering method, a deposition method or the like, and patterning carried out so that the first electrode 14 takes a predetermined shape.

Next, as illustrated in FIG. 10(c), the piezoelectric layer 15 is layered on the first electrode 14 and patterning carried out. It is possible to form a piezoelectric layer 15 using a chemical solution deposition (CSD) method in which a piezoelectric material formed of a metal oxide is obtained by coating and drying a metal complex is in which a metal complex is dissolved and dispersed in a solvent and further baking at a high temperature. There is no limitation to the CSD method, and a sol-gel method, a laser ablation method, a sputtering method, a pulse laser deposition method (PLD) method, a CVD method, an aerosol deposition method and the like may be used.

Next, as illustrated in FIG. 11(a), the second electrode 16 is formed by a sputtering method, a thermal oxidation method or the like on the piezoelectric layer 15 and subjected to patterning, and the piezoelectric element 17 formed of the first electrode 14, the piezoelectric layer 15, and the second electrode 16 is formed.

Next, as illustrated in FIG. 11(b), the bypass wiring 21 and the second bypass wiring 22 are formed by forming an adhesive layer of nickel, chromium or the like and a metal layer, and carrying out patterning. As illustrated in FIG. 11(c), an opening portion 18 is formed, thereby forming the ultrasound sensor 1.

In this way, through manufacturing with a separate process to the thin-film manufacturing process of the ultrasound sensor element 10, it is possible for the yield through manufacturing to be improved and possible to form the wiring with different materials and cross-sectional areas to the first electrode 14 and the second electrode 16. For the bypass wiring 21, the product of the Young's modulus, the film thickness and the wiring width (below, also referred to as a value) is greater than that of the second electrode 16, and the electric resistance value per unit length of the material which forms the wiring (below, also simply referred to as electric resistance value) is lower than that of the second electrode 16. Accordingly, it is conversely possible to suppress the α value of the second electrode 16 to be small and to increase the second electrode 16, and possible to reduce the impedance of the bypass wiring 21 while suppressing a lowering of the displacement of the piezoelectric element 17 due to the wiring. The same applies to the second bypass wiring 22.

In a region in the ultrasound sensor 1 in which the bypass wiring 21 and the first electrode 14 or the second electrode 16 are superimposed, it is possible for the yield during manufacturing to be improved by proving the bypass wiring 21 above the first electrode 14 or the second electrode 16, and possible for the reliability to be improved. However, the structure of the ultrasound sensor 1 is not limited thereto.

Other Embodiments

Although not described in each of the above-described embodiments, it is possible to use a configuration in which the opposite side to the piezoelectric element 17 of the diaphragm 50 becomes a pass-through region for ultrasonic waves transmitted towards a measurement target or ultrasound waves reflected from the measurement target (echo signal). Accordingly, it is possible to simplify the configuration of the opposite side to the piezoelectric element 17 of the diaphragm 50, and possible to ensure a favorable pass-through region for ultrasonic waves and the like. An electrical region of the electrodes, wirings and the like and the contact and fixing region of each member is distanced from the measurement target, and it becomes easier to prevent contamination or leakage current between these and the measurement target. Accordingly, it is possible to also favorably apply the invention a medical device which is particularly averse to contamination or leakage current, for example, ultrasound diagnostic equipment, blood pressure gages, and eye pressure gages.

In the embodiment described above, although the bypass wirings 21 and 23, the second bypass wirings 22 and 24 are provided on the same plane as the first electrode 14 and the second electrode 16, there is no limitation thereto, the bypass wiring may be three-dimensionally connected for each group of first electrodes or second electrodes shared per predetermined group or for each plurality of groups. For example, the bypass wiring may be connected via a probe terminal or the like to the shared first electrode 14 or the second electrode 16, or may be connected via wire bonding or the like.

Furthermore, although not described in the above-described embodiments, it is preferable that a sealing plate that seals the region which includes the piezoelectric element 17 is bonded to the substrate 11. Thereby, because it is possible to physically protect the piezoelectric element 17, and the strength of the ultrasound sensor 1 also increases, it is possible to increase the structural stability. It is possible for the handling properties of the ultrasound sensor 1 which includes the piezoelectric elements 17 to be improved in a case where the piezoelectric elements 17 are formed as thin films.

In the above-described embodiment, although an example is given in which the opening portion 18 is formed for each piezoelectric element 17, there is no limitation thereto, and the openings may be formed corresponding to a plurality of piezoelectric elements 17. For example, an opening which is shared by a row of piezoelectric elements 17 arranged along the scanning direction may be provided or one opening may be formed for all piezoelectric elements 17. Although the vibration states of the piezoelectric elements 17 become different in a case where an opening shared for a plurality of piezoelectric elements 17 is provided, a pressing member or the like is provided between each of the piezoelectric elements 17 from the opposite side to the substrate 11 of the diaphragm, and similar vibration may be performed as a case where independent openings are provided.

Figure 12:
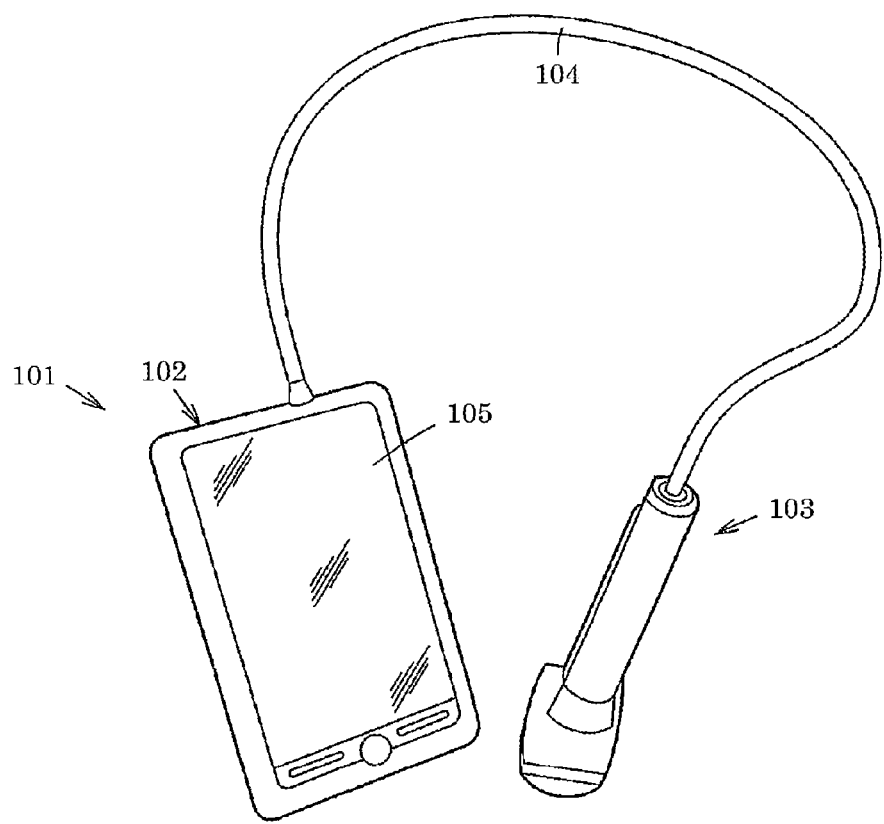
FIG. 12 is a perspective view illustrating an example of an ultrasonic diagnostic apparatus.
Figure 13:
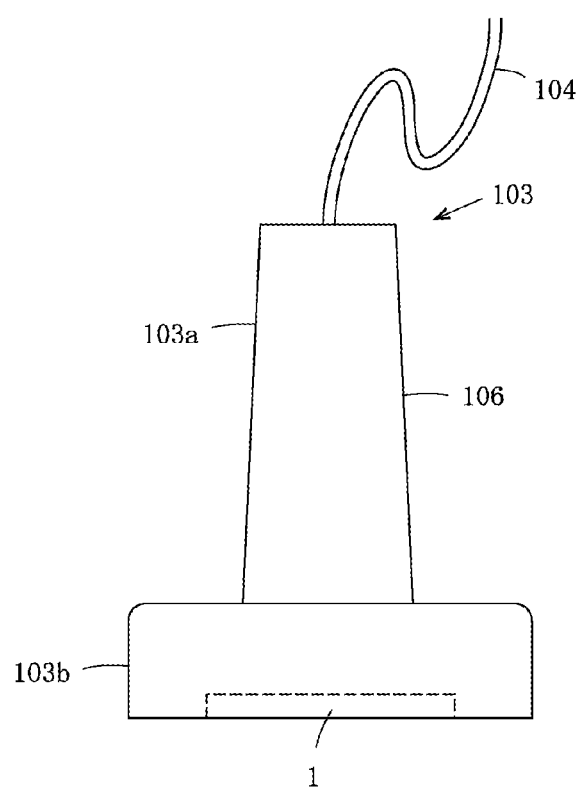
FIG. 13 is a perspective view illustrating an example of an ultrasound probe.

Here, an example of an ultrasonic diagnostic apparatus using the ultrasound sensor described above will be described. FIG. 12 is a perspective view illustrating a schematic configuration of an example of the ultrasonic diagnostic apparatus, and FIG. 13 is a cross-sectional vies illustrating the ultrasound probe.

As illustrated in the drawings, the ultrasonic diagnostic apparatus 101 is provided with a device terminal 102 and an ultrasound probe (probe) 103. The device terminal 102 and the ultrasound probe 103 are connected by a cable 104. The device terminal 102 and the ultrasound probe 103 exchange electrical signals through the cable 104. A display panel (display device) 105 is incorporated in the device terminal 102. A screen of the display panel 105 is exposed in the surface of the device terminal 102. In the device terminal 102, an image is generated based on ultrasonic waves transmitted from the ultrasound sensor 1 of the ultrasound probe 103 and detected. The imaged detection results are displayed on the screen of the display panel 105.

The ultrasound probe 103 includes a housing 106. The ultrasound sensor 1 in which a plurality of ultrasound sensor elements 10 are two-dimensionally arranged in the first direction X and the second direction Y is stored in the housing 106. The ultrasound sensor 1 is provided so that the surface thereof is exposed in the surface of the housing 106. The ultrasound sensor 1 outputs ultrasonic wave s from the surface and receives the reflected waves of the ultrasound. It is possible to provide the ultrasound probe 103 with a probe head 103b which is freely detachable from the probe main body 103a. At this time, it is possible for the ultrasound sensor 1 to be incorporated in the housing 106 of the probe head 103b. The ultrasound sensor 1 is formed with the ultrasound sensor elements 10 arranged two-dimensionally in the first direction X and the second direction Y.

The invention claimed is:

1. An ultrasound sensor, comprising:
a plurality of ultrasound elements which include a first electrode, a piezoelectric layer, and a second electrode and which are arranged in a first direction and a second direction,
wherein at least a portion of the plurality of ultrasound elements are grouped,
at least one of the first electrode and the second electrode is shared for each of the grouped ultrasound elements,
bypass wiring is connected to one of the shared first electrode and second electrode, an α value of the bypass wiring is greater than the α value of the first electrode or second electrode to which the bypass wiring is connected, and when electric resistance values per unit length are compared, the electric resistance value of the bypass wiring is lower than the electrical resistance value of the first electrode or the second electrode to which the bypass wiring is connected to; wherein α value=(Young's modulus of Constituent Material)×(cross-sectional area of wiring or electrode).

2. The ultrasound sensor according to claim 1, wherein the bypass wiring is provided above the first electrode or the second electrode in a region in which the bypass wiring and the first electrode or the second electrode are superimposed.

3. The ultrasound sensor according to claim 1, wherein the other of the shared first electrode and the second electrode is also shared, second bypass wiring that is electrically connected to the other of the first electrode or the second electrode is provided, and the α value of the second bypass wiring is greater than that of the first electrode or the second electrode on which the bypass wiring is connected.

4. The ultrasound sensor according to claim 1, wherein the bypass wiring is formed of a different material to the first electrode or the second electrode.

5. A method of manufacturing an ultrasound sensor that includes a plurality of ultrasound elements that include a first electrode, a piezoelectric layer, and a second electrode, and which are arranged in a first direction and a second direction and at least one of the first electrode and the second electrode is shared for each of the plurality of ultrasound elements, the method comprising:

forming bypass wiring that is provided with respect to the first electrode or the second electrode after forming the first electrode, the piezoelectric layer, and the second electrode, and for which an α value is greater than that of the first electrode or the second electrode and the electrical resistance value per unit length is lower than that of the first electrode or the second electrode; wherein α value=(Young's modulus of Constituent Material)×(cross-sectional area of wiring or electrode).

6. The ultrasound sensor according to claim 2, wherein the other of the shared first electrode and the second electrode is also shared, second bypass wiring that is electrically connected to the other of the first electrode or the second electrode is provided, and the α value of the second bypass wiring is greater than that of the first electrode or the second electrode on which the bypass wiring is connected.

7. The ultrasound sensor according to claim 2, wherein the bypass wiring is formed of a different material to the first electrode or the second electrode.

8. The ultrasound sensor according to claim 3, wherein the bypass wiring is formed of a different material to the first electrode or the second electrode.

9. The ultrasound sensor according to claim 6, wherein the bypass wiring is formed of a different material to the first electrode or the second electrode.

* * * * *